United States Patent [19]

Ienaga et al.

[11] Patent Number: 4,683,240
[45] Date of Patent: Jul. 28, 1987

[54] PHARMACEUTICAL COMPOSITION CONTAINING AN IMIDAZOLIDINETRIONE DERIVATIVE OR PHARMACEUTICALLY ACCEPTABLE SALT THEREOF

[75] Inventors: Kazuharu Ienaga; Ko Nakamura; Akira Ishii, all of Hyogo, Japan

[73] Assignee: Nippon Zoki Pharmaceutical Co., Ltd., Osaka, Japan

[21] Appl. No.: 826,607

[22] Filed: Feb. 6, 1986

[30] Foreign Application Priority Data

Feb. 6, 1985 [JP] Japan .................................. 60-22559

[51] Int. Cl.$^4$ ......................................... A61K 31/415
[52] U.S. Cl. .................................. 514/390; 514/824; 514/866
[58] Field of Search ......................................... 514/390

[56] References Cited
U.S. PATENT DOCUMENTS 3,418,334  12/1968  Stoffel .................................. 548/307

Primary Examiner—Frederick E. Waddell
Attorney, Agent, or Firm—Birch, Stewart, Kolasch & Birch

[57] ABSTRACT

Pharmaceutical compositions containing imidazolidinetrione derivatives or pharmaceutically acceptable salts thereof having hypoglycemic and hypolipidemic effects. The compositions comprise as an active ingredient at least one imidazolidinetrione derivative of the formula:

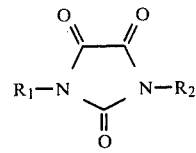

wherein each of $R_1$ and $R_2$, which may be the same or different, is hydrogen, an alkyl group, a cycloalkyl group or

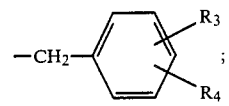

and each of $R_3$ and $R_4$, which may be the same or different, is hydrogen, halogen, a nitro group, a lower alkyl group or a lower alkoxy group.

9 Claims, No Drawings

PHARMACEUTICAL COMPOSITION CONTAINING AN IMIDAZOLIDINETRIONE DERIVATIVE OR PHARMACEUTICALLY ACCEPTABLE SALT THEREOF

DETAILED DESCRIPTION OF THE INVENTION

The present invention relates to pharmaceutical compositions containing imidazolidinetrione derivatives or pharmaceutically acceptable salts thereof having hypoglycemic and hypolipidemic effects.

An abnormal increase or unbalance of blood glucose or lipids causes various morbid symptoms. Diabetes causes acidosis inducing diabetic coma, microangiopathy such as retiopathy or nephrosis, and promotes arteriosclerosis. Hyperlipidemia is not only a direct cause of arteriosclerosis but also causes the development of various symptoms such as ischemic heart disease, and often involves the complication of diabetes.

Oral sulfonylureas and biguanides having a hypoglycemic effect have been conventionally used for the treatment of diabetes, but they tend to promote certain side effects such as excessive hypoglycemia and lactic acidosis. Insulin, a well-known antidiabetic, can only be administered intravenously due to its chemical nature, and therefore, is troublesome and inconvenient to use.

As a result of the investigations for orally administrable hypoglycemic compounds having greater safety that known compounds to solve the problem mentioned above, the inventors have found that imidazolidinetrione derivatives and pharmaceutically acceptable salts thereof have an excellent hypoglycemic effect, i.e., they lower the abnormally high level of blood glucose to the normal level without excessive hypoglycemia, as well as low toxicity and great safety.

An object of the present invention is to provide pharmaceutical compositions containing imidazolidinetrione derivatives or pharmaceutically acceptable salts thereof as an active ingredient, which are useful as orally administrable drugs to treat and prevent diabetics and/or hyperlipidemia, and also various diseases caused by them.

The present invention relates to pharmaceutical compositions containing at least one imidazolidinetrione derivative or a pharmaceutically acceptable salt thereof represented by the following formula (I):

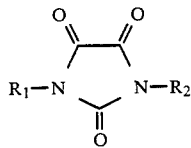

wherein each of $R_1$ and $R_2$, which may be the same or different, is hydrogen, an alkyl group, a cycloalkyl group or

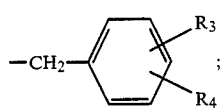

and each of $R_3$ and $R_4$, which may be the same or different, is hydrogen, halogen, a nitro group, a lower alkyl group or a lower alkoxy group.

Each of $R_1$ and $R_2$, which may be the same or different, is hydrogen, an alkyl group, preferably a straight or branched alkyl group having 1 to 20 carbon atoms, such as methyl, ethyl, propyl, iso-propyl, butyl, iso-butyl, sec-butyl, tert-butyl, pentyl, iso-pentyl, neo-pentyl, tert-pentyl, hexyl, iso-hexyl, dimethylbutyl, heptyl, octyl, nonyl, decyl or stearyl; a cycloalkyl group, preferably having 3 to 8 carbon atoms such as cyclopropyl, cyclobutyl, cyclopentyl, cyclohexyl, cycloheptyl or cyclooctyl;

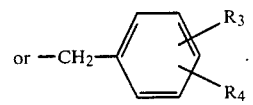

When one of $R_1$ and $R_2$ is

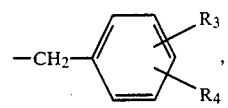

the other substituent is preferably hydrogen.

Each of $R_3$ and $R_4$, which may be the same or different, is hydrogen, halogen, such as fluoride, chloride or bromide, a lower alkyl group, preferably a straight or branched alkyl group having 1 to 4 carbon atoms, such as methyl, ethyl, propyl, iso-propyl, butyl, iso-butyl, sec-butyl, tert-butyl, or a lower alkoxy group, preferably a straight or branched alkoxy group having 1 to 4 carbon atoms, such as methoxy, ethoxy, propoxy, iso-propoxy, butoxy, iso-butoxy, sec-butoxy, or tert-butoxy.

The imidazolidinetrione derivatives include not only novel compounds but also known compounds. However, it has not been reported that such compounds have hypoglycemic and hypolipidemic effects.

Preferred compounds of the present invention are indicated as follows:
  imidazolidinetrione
  1-methylimidazolidinetrione
  1-ethylimidazolidinetrione
  1-butylimidazolidinetrione
  1-iso-butylimidazolidinetrione
  1-tert-butylimidazolidinetrione
  1-hexylimidazolidinetrione
  1-(1,3-dimethyl)butylimidazolidinetrione
  1-decylimidazolidinetrione
  1-cyclopentylimidazolidinetrione
  1-cyclohexylimidazolidinetrione
  1,3-dimethylimidazolidinetrione
  1-cyclopentyl-3-ethylimidazolidinetrione
  1,3-dicyclohexylimidazolidinetrione
  1-benzylimidazolidinetrione
  1-(2-fluorobenzyl)imidazolidinetrione
  1-(3-fluorobenzyl)imidazolidinetrione
  1-(4-fluorobenzyl)imidazolidinetrione
  1-(2-chlorobenzyl)imidazolidinetrione
  1-(4-chlorobenzyl)imidazolidinetrione
  1-(4-bromobenzyl)imidazolidinetrione
  1-(3-nitrobenzyl)imidazolidinetrione
  1-(4-nitrobenzyl)imidazolidinetrione
  1-(2-methylbenzyl)imidazolidinetrione
  1-(3-methylbenzyl)imidazolidinetrione
  1-(4-methylbenzyl)imidazolidinetrione 1-(2-methoxybenzyl)imidazolidinetrione
1-(3-methoxybenzyl)imidazolidinetrione
1-(4-methoxybenzyl)imidazolidinetrione
1-(3,4-dimethoxybenzyl)imidazolidinetrione
1-(3,4-dichlorobenzyl)imidazolidinetrione The imidazolidinetrione derivatives of the present invention include pharmaceutically acceptable salts of the compounds of the above-mentioned formula (I) with alkali metals such as sodium or potassium, with alkaline earth metals such as calcium, magnesium or barium, with other metals such as aluminum, or with organic bases such as ammonium or organic amines.

In addition, the imidazolidinetrione derivatives of the invention include their metal complexes, for example, complexes with zinc, iron, etc.

These salts can be prepared from free imidazolidinetrione derivatives or other salts of these derivatives by known methods.

When optical isomers exist in the compounds of the present invention, the present invention includes any of the dl-, l- and d-isomers.

The imidazolidinetrione derivatives of the present invention can be prepared by art-recognized methods. [T. Yonezawa et al, Nippon Kagaku Zasshi, 89, No. 8, 62–64 (1968), Tad L. Patton, J. Org. Chem., 32, No. 2, 383–388 (1967), etc.]

(1) Oxalyl chloride and an N-substituted urea, such as N-alkylurea, N-cycloalkylurea, N-benzylurea, N-halogenated benzylurea, N-nitrobenzylurea, N-alkylbenzylurea or N-alkoxybenzylurea, were stirred in an appropriate solvent such as tetrahydrofuran which does not inhibit the reaction in an ice-water bath or at room temperature; or diethyl oxalate and the above-mentioned N-substituted urea were stirred in an appropriate solvent which does not inhibit the reaction in the presence of an organic base such as an amine or alkali metal alkoxide at room temperature, if desired, by heating to higher temperatures to give the imidazolidinetrione derivatives of the present invention.

(2) The compounds of the invention can also be prepared by usual N-alkylation wherein unsubstituted, 1-alkylsubstituted or 1-cycloalkylsubstituted imidazolidinetrione is reacted with halogenated alkyl.

The resultant compounds of the present invention are purified by usual methods such as distillation, chromatography and recrystallization. They are identified by elemental analysis, melting point, IR, NMR, UV and mass spectrum.

The following examples, which are illustrative describe the preparation of the compounds of the present invention.

EXAMPLE 1-methylimidazolidinetrione (compound 2)
m.p.: 153°–155° C.
IR(KBr): 3210, 1790, 1740, 1718, 1460 cm$^{-1}$.
NMR(DMSO-d$_6$): $\delta=2.92$(s, 3H), 11.98(brs, 1H).
MS (m/z): 128 (M+), 100, 56, 44.

1-ethylimidazolidinetrione (compound 3)
m.p.: 123°–125° C.
IR(KBr): 3200, 2960, 1810, 1785, 1720, 1060 cm$^{-1}$.
NMR(DMSO-d$_6$): $\delta=1.13$(t, 3H, J=7 Hz), 3.47(q, 2H, J=7 Hz), 11.96(brs, 1H).
MS (m/z): 142 (M+), 71, 56, 43.

1-butylimidazolidinetrione (compound 4)
m.p.: 97°–99° C.
IR(KBr): 3200, 2950, 1800, 1785, 1718, 1445 cm$^{-1}$.
NMR(DMSO-d$_6$): $\delta=0.88$(t, 3H, J=7 Hz), 1.29(qt, 2H, J$_1$=7 Hz, J$_2$=7 Hz), 1.52(tt, 2H, J$_1$=7 Hz, J$_2$=7 Hz), 3.43(t, 2H, J=7 Hz), 11.97 (brs, 1H).
MS (m/z): 170 (M+), 128, 115, 99, 70, 56, 41.

1-iso-butylimidazolidinetrione (compound 5)
m.p.: 145°–147° C.
IR(KBr): 3170, 2950, 2860, 1800, 1730, 1710 cm$^{-1}$.
NMR(DMSO-d$_6$): $\delta=0.85$(d, 6H, J=6.4 Hz), 1.90 m, 1H), 3.23(d, 2H, J=6.8 Hz), 11.98(s, 1H).
MS (m/z): 170 (M+), 128, 115, 56, 43, 41, 27.

1-tert-butylimidazolidinetrione (compound 6)
m.p.: 121°–124° C.
IR(KBr): 3170, 1798, 1701, 1366, 1322 cm$^{-1}$.
NMR(DMSO-D$_6$): $\delta=1.51$(s, 9H), 11.84(brs, 1H).
MS (m/z): 170 (M+), 155, 114, 84, 57, 41.

1-hexylimidazolidinetrione (compound 7)
m.p.: 99°–101° C.
IR(KBr): 3200, 2950, 2920, 2850, 1810, 1790, 1720 cm$^{-1}$.
NMR(DMSO-d$_6$): $\delta=0.85$(t, 3H, J=6.8 Hz), 1.24(s, 6H), 1.50(tt, 2H, J$_1$=7.8 Hz, J$_2$=6.8 Hz), 3.40(t, 2H, J=6.8 Hz), 11.95(s, 1H).
MS (m/z): 198 (M+), 128, 116, 115, 84, 56, 55, 43, 41, 27.

1-(1,3-dimethylbutyl)imidazolidinetrione (compound 8)
m.p.: 61°–65° C.
IR(KBr): 3300, 2950, 2860, 1800, 1720 cm$^{-1}$.
NMR(DMSO-d$_6$): $\delta=0.82$(d, 3H, J=6.4 Hz), 0.83(d, 3H, J=6.4 Hz), 1.29(d, 3H, J=6.8 Hz), 1.36(m, 1H), 1.51(m, 1H), 1.83(m, 1H), 4.12(m, 1H), 11.94(s, 1H).
MS (m/z): 198 (M+), 183, 141, 116, 115, 84, 83, 70, 69, 57, 43, 41, 27.

1-decylimidazolidinetrione (compound 9)
m.p.: 110°–112° C.
IR(KBr): 3200, 2950, 2920, 2850, 1820, 1790, 1730, 1710 cm$^{-1}$.
NMR(DMSO-d$_6$): $\delta=0.84$(t, 3H, J=7.2 Hz), 1.23(s, 14H), 1.51(m, 2H), 3.40(t, 2H, J=7.2 Hz), 11.95(s, 1H).
MS (m/z): 254 (M+), 142, 128, 116, 83, 69, 55, 43, 41, 27.

1-cyclopentylimidazolidinetrione (compound 10)
m.p.: 98°–100° C.
IR(KBr): 3540, 3250, 2945, 2700, 1760, 1725, 1420, 1100 cm$^{-1}$.
NMR(DMSO-d$_6$): $\delta=1.4$–1.6(m, 2H), 1.6–2.0(m, 6H), 4.34(tt, 1H, J$_1$=7.4 Hz, J$_2$=7.4 Hz), 11.90(brs, 1H).
MS (m/z): 182 (M+), 141, 116, 67, 41.

1-cyclohexylimidazolidinetrione compound 11)
m.p.: 190°–191° C.
IR(KBr): 3180, 2920, 1795, 1730, 1410 cm$^{-1}$.
NMR(DMSO-d$_6$): $\delta=1.0$–1.4(m, 4H), 1.5–2.0(m, 6H), 3.9(m, 1H), 11.93(brs, 1H).
MS (m/z: 196 (M+), 128, 116, 82, 67, 55, 41.

1,3-dimethylimidazolidinetrione (compound 12)
m.p.: 152°–153° C.
IR(KBr): 2940 1760, 1730, 1705, 1468, 1300 cm$^{-1}$.
NMR(DMSO-d$_6$): $\delta=2.97$(s, 6H).
MS (m/z): 142 (M+), 114, 86, 70, 58.

1-cyclopentyl-3-ethylimidazolidinetrione (compound 13)
m.p.: 54°–56° C.
IR(KBr): 2940, 2855, 1770, 1715, 1418, 1120, 558 cm$^{-1}$.
NMR(DMSO-d$_6$): $\delta=1.12$(t, 3H, J=7.4 Hz), 1.4–1.6(m, 2H), 1.6–2.0(m, 6H), 3.48(q, 2H, J=7.4 Hz), 4.37(tt, 1H, J$_1$=8.0 Hz, J$_2$=8.0 Hz).
MS (m/z): 210 (M+), 144, 115, 68, 41.

1,3-dicyclohexylimidazolidinetrione (compound 14)
m.p.: 176°–178° C.
IR(KBr): 2925, 2850, 1760, 1728, 1410, 758 cm$^{-1}$.
NMR(DMSO-d$_6$): δ=1.0–1.2(m, 2H), 1.2–1.4(m, 4H), 1.4–2.0(m, 14H), 3.81(tt, 2H, J$_1$=3.7 Hz, J$_2$=12.5 Hz).
MS (m/z): 278 (M+), 197, 115, 83, 67, 55, 41.

1-benzylimidazolidinetrione (compound 15)
m.p.: 169°–170° C.
IR(KBr): 3430, 3200, 1790, 1735 cm$^{-1}$.
NMR(DMSO-d$_6$): δ=4.62(s, 2H), 7.24–7.33(m, 5H), 12.08(s, 1H).
MS (m/z): 204 (M+), 176, 147, 133, 91, 77, 65, 51.

1-(2-fluorobenzyl)imidazolidinetrione (compound 16)
m.p.: 196°–197° C.
IR(KBr): 3430, 3200, 3070, 1795, 1730, 1590 cm$^{-1}$.
NMR(DMSO-d$_6$): δ=4.66(s, 2H), 7.14–7.46(m, 4H), 12.11(s, 1H).
MS (m/z): 222 (M+), 165, 151, 123, 109, 83, 70, 63, 51, 50, 43.

1-(3-fluorobenzyl)imidazolidinetrione (compound 17)
m.p.: 166°–167° C.
IR(KBr): 3430, 3200, 1790, 1735, 1590 cm$^{-1}$.
NMR(DMSO-d$_6$): δ=4.65(s, 2H, 7.07–7.40(m, 4H), 12.08(s, 1H).
MS (m/z): 222 (M+), 165, 151, 122, 109, 83, 70, 63, 51, 50, 43.

1-4-fluorobenzyl)imidazolidinetrione (compound 18)
m.p.: 182°–183° C.
IR(KBr): 3440, 3200, 3070, 1790, 1730, 1600 cm$^{-1}$.
NMR(DMSO-d$_6$): δ=4.61(s, 2H), 7.12–7.40(m, 4H), 12.06(s, 1H).
MS (m/z): 222 (M+), 165, 151, 122, 109, 95, 83, 70, 63, 51, 50, 43.

1-(2-chlorobenzyl)imidazolidinetrione (compound 19)
m.p.: 192°–193° C.
IR(KBr): 3180, 3100, 1780, 1730 cm$^{-1}$.
NMR(DMSO-d$_6$): δ=4.68(s, 2H), 7.28–7.50(m, 4H), 12.17(s, 1H).
MS (m/z): 238 (M+), 203, 167, 132, 125, 89, 77, 70, 63, 51, 50, 43.

1-(4-chlorobenzyl)imidazolidinetrione (compound 20)
m.p.: 177°–178° C.
IR(KBr): 3240, 3075, 1780, 1730 cm$^{-1}$.
NMR(DMSO-d$_6$): δ=4.62(s, 2H), 7.35–7.40(m, 4H), 12.08(s, 1H).
MS (m/z): 238 (M+), 181, 167, 132, 125, 89, 77, 70, 63, 51, 50, 43.

1-(4-bromobenzyl)imidazolidinetrione (compound 21)
m.p.: 192°–193° C.
IR(KBr): 3430, 3130, 3050, 1795, 1720 cm$^{-1}$.
NMR(DMSO-d$_6$): δ=4.60(s, 2H), 7.52(dt, 2H, J$_1$=2.0 Hz, J$_2$=8.4 Hz), 7.30(dt, 2H, J$_1$=2.0 Hz, J$_2$=8.4 Hz), 12.07(s, 1H).
MS (m/z): 282 (M+), 225, 211, 169, 132, 90, 77, 70, 63, 51, 50, 43.

1-(3-nitrobenzyl)imidazolidinetrione (compound 22)
m.p.: 139°–140° C.
IR(KBr): 3430, 3230, 1790, 1730, 1535 cm$^{-1}$.
NMR(DMSO-d$_6$): δ=4.78(s, 2H), 7.63(t, 1H, J=8.0 Hz), 7.82(d, 1H, J=8.0 Hz), 8.13–8.14(m, 1H), 8.24(t, 1H, J=2.0 Hz), 12.08(s, 1H).
MS (m/z): 249 (M+), 232, 178, 161, 136, 132, 125, 89, 77, 70, 63, 51, 50, 43.

1-(4-nitrobenzyl)imidazolidinetrione (compound 23)
m.p.: 202°–204° C.
IR(KBr): 3440, 3230, 1780, 1730, 1515 cm$^{-1}$.
NMR(DMSO-d$_6$): δ=4.78(s, 2H), 7.65(d, 2H, J=8.0 Hz), 8.18(dt, 2H, J$_1$=2.0 Hz, J$_2$=8.8 Hz), 12.12(s, 1H).
MS (m/z): 249 (M+), 219, 178, 132, 106, 89, 78, 77, 70, 63, 51, 50.

1-(2-methylbenzyl)imidazolidinetrione (compound 24)
m.p.: 195°–196° C.
IR(KBr): 3430, 3170, 3080, 1770, 1730 cm$^{-1}$.
NMR(DMSO-d$_6$): δ=2.32(s, 3H), 4.59(s, 2H), 7.10–7.27(m, 4H), 12.09(s, 1H).
MS (m/z): 218 (M+), 147, 104, 91, 77, 65, 51, 43.

1-(3-methylbenzyl)imidazolidinetrione (compound 25)
m.p.: 149°–150° C.
IR(KBr): 3220, 1780, 1760, 1725, 1600 cm$^{-1}$.
NMR(DMSO-d$_6$): δ=2.27(s, 3H), 4.58(s, 2H), 7.07–7.22(m, 4H), 12.07(s, 1H).
MS (m/z): 218 (M+), 147, 132, 105, 91, 77, 65, 51, 43.

1-(4-methylbenzyl)imidazolidinetrione (compound 26)
m.p.: 177°–178° C.
IR(KBr): 3450, 3180, 1800, 1725 cm$^{-1}$.
NMR(DMSO-d$_6$): δ=2.26(s, 3H), 4.57(s, 2H), 7.12(d, 2H, J=8.0 Hz), 7.20(d, 2H, J=8.0 Hz), 12.07(s, 1H).
MS (m/z): 218 (M+), 161, 147, 132, 105, 91, 77, 65, 51.

1-(2-methoxybenzyl)imidazolidinetrione (compound 27)
m.p.: 171°–172° C.
IR(KBr): 3430, 3200, 1805, 1790, 1720, 1600 cm$^{-1}$.
NMR(DMSO-d$_6$): δ=3.80(s, 3H), 4.57(s, 2H), 6.87(dt, 1H, J$_1$=0.8 Hz, J$_2$=7.6 Hz), 6.99(d, 1H, J=8.0 Hz), 7.23–7.28(m, 2H).
MS (m/z): 234 (M+), 163, 148, 134, 121, 91, 77, 65, 51, 43.

1-(3-methoxybenzyl)imidazolidinetrione (compound 28)
m.p.: 142°–143° C.
IR(KBr): 3210, 2940, 1790, 1735, 1595 cm$^{-1}$.
NMR(DMSO-d$_6$): δ=3.72(s, 3H), 4.59(s, 2H), 6.82–7.25(m, 4H), 12.07(s, 1H).
MS (m/z): 234 (M+), 167, 148, 121, 91, 77, 65, 51, 43.

1-(4-methoxybenzyl)imidazolidinetrione (compound 29)
m.p.: 172°–173° C.
IR(KBr): 3430, 3190, 2850, 1790, 1730, 1585 cm$^{-1}$.
NMR(DMSO-d$_6$): δ=3.72(s, 3H), 4.55(s, 2H), 6.87(dt, 2H, J$_1$=2.4 Hz, J$_2$=8.8 Hz), 7.25(dt, 2H, J$_1$=2.4 Hz, J$_2$=8.8 Hz), 12.05(s, 1H).
MS (m/z): 234 (M+), 177, 163, 148, 121, 91, 77, 65, 51, 43.

1-(3,4-dimethoxybenzyl)imidazolidinetrione (compound 30)
m.p.: 171°–174° C.
IR(KBr): 3420, 3250, 2950, 2840, 1780, 1740, 1590 cm$^{-1}$.
NMR(DMSO-d$_6$): δ=3.71(s, 3H), 3.72(s, 3H), 4.54(s, 2H), 6.82–6.89(m, 3H), 12.03(s, 1H).
MS (m/z): 264 (M+), 234, 178, 151, 121, 107, 91, 77, 65, 51.

1-(3,4-dichlorobenzyl)imidazolidinetrione (compound 31)
m.p.: 172°–173° C.
IR(KBr): 3430, 3200, 1790, 1735 cm$^{-1}$.
NMR(DMSO-d$_6$): δ=4.64(s, 2H), 7.35(dd, 1H, J$_1$=2.0 Hz, J$_2$=8.0 Hz), 7.59(d, 1H, J=8.0 Hz), 7.66(d, 1H, J=2.0 Hz), 12.06(s, 1H).
MS (m/z): 272 (M+), 215, 201, 166, 159, 123, 89, 70, 43.

The compounds of the present invention may be produced by each of the above-mentioned preparations, however, these examples do not limit the preparations of the compounds of the present invention.

The following description serves to illustrate pharmaceutical studies of the compounds of the present invention.

(1) Acute toxicity test

The test compounds of the present invention suspended in 0.5% aqueous solution of carboxymethylcellulose (C.M.C.) were orally administered to groups of 4 to 6 ddY-strain male mice (weighing about 19 g) which had fasted for 20 hours. The lethal dose was determined by the number of deaths for 7 days thereafter.

An example of the results is shown in Table 1.

TABLE 1

| Test Compound | $LD_{50}$ (mg/kg) |
|---|---|
| compound 2 | about 900 |
| compound 3 | about 700 |
| compound 15 | about 1,000 |

(2) Hypoglycemic effect

Groups of 7 Wistar-strain male rats (weighing about 200 g) which were fasted for 18 hours were used for measurement of hypoglycemic effect according to the modified method by Dulin et al. [Dulin, W. L. et al., Proc. Soc. Expl. Med., 107, 245 (1961)]. That is, 0.5 ml/100 g of 20% aqueous solution of glucose was subcutaneously administered to the backs of rats to prevent a decrease in blood glucose level because of the fasting. Immediately thereafter the test drug suspended in 0.5% aqueous C.M.C. solution was orally given, and 2 hours later, the animals underwent laparotomy under pentobarbital anesthesia, then blood was drawn from the vena cava. The obtained blood sample was allowed to stand for 30 minutes to complete the coagulation and was centrifuged to obtain the serum. Blood sugar level was measured according to the mutalotase GOD method [Trinder, Ann. Clin. Biochem., 6, 24 (1979)]. Asterisks indicate significant differences (*: $p<0.05$, : $p<0.01$, *: $p<0.001$) from the control.

Results are shown in Tables 2 and 3.

TABLE 2

| Test Compound | Dosage (mg/kg) | Blood Glucose Level (mg/dl) | Decrease (%) |
|---|---|---|---|
| control | — | 133 ± 6 | — |
| compound 2 | 12.5 | 109 ± 5** | 18.0 |
|  | 25 | 99 ± 2** | 25.6 |
|  | 50 | 91 ± 4*** | 31.6 |
|  | 100 | 99 ± 5** | 25.6 |
| compound 3 | 100 | 100 ± 2** | 24.8 |
| compound 4 | 100 | 88 ± 7*** | 33.8 |
| compound 5 | 100 | 81 ± 1** | 39.1 |
| compound 6 | 100 | 109 ± 4* | 18.0 |
| compound 7 | 100 | 102 ± 6*** | 23.3 |
| compound 9 | 100 | 109 ± 4** | 18.0 |
| compound 10 | 100 | 100 ± 4*** | 24.8 |
| compound 11 | 100 | 101 ± 2*** | 24.1 |
| compound 12 | 100 | 115 ± 4*** | 15.0 |
| compound 13 | 100 | 116 ± 5*** | 14.7 |
| Tolubutamide | 100 | 48 ± 1*** | 63.9 |

TABLE 3

| Test Compound | Dosage (mg/kg) | Blood Glucose Level (mg/dl) | Decrease (%) |
|---|---|---|---|
| control | — | 133 ± 4 | — |
| compound 15 | 100 | 112 ± 3** | 15.8 |
| compound 16 | 100 | 118 ± 4* | 11.3 |
| compound 17 | 100 | 115 ± 2** | 13.5 |
| compound 18 | 100 | 106 ± 3*** | 20.3 |
| compound 23 | 100 | 117 ± 3** | 12.0 |

TABLE 3-continued

| Test Compound | Dosage (mg/kg) | Blood Glucose Level (mg/dl) | Decrease (%) |
|---|---|---|---|
| compound 24 | 100 | 116 ± 3** | 12.8 |
| compound 25 | 100 | 115 ± 3** | 13.5 |
| compound 26 | 100 | 120 ± 2* | 9.8 |
| compound 29 | 100 | 120 ± 2* | 9.8 |

(3) Hypolipidemic effect

The test drugs suspended in 0.5% aqueous C.M.C. solution were orally administered to groups of 8 Wistar-strain male rats (weighing about 185 g) which were fasted for 18 to 20 hours. 2 hours later, the serum was obtained in the same manner described in (2). Serum triglyceride was measured according to the GPO-p-chlorophenol colorimetric determination [Richard W. Spayd et al., Clinical Chemistry, 24, 1343 (1978)], serum free fatty acid was measured according to the Acyl CoA Synthetase-Acyl CoA Oxidase method [Shimizu S. et al., Biochem. Biophys. Res. Commun., 91, 108 (1979)], free fatty acid was measured according to the enzymatic method [Charles C. Allain et al., Clin. Chem., 20, No. 4, 470 (1974)] and total cholesterol was measured according to the enzymatic method [Takayama M. et al., Clinica Chimica Acta, 79, 93 (1977)]. Asterisks indicate significant differences (*: $p<0.05$, : $p<00.01$, *: $p<0.001$) from the control.

Results are shown in Tables 4 to 7.

TABLE 4

| Test Compound | Dosage (mg/kg) | Serum Triglyceride Level (mg/dl) | Decrease (%) |
|---|---|---|---|
| control | — | 65 ± 5 | — |
| compound 2 | 100 | 22 ± 1*** | 66.2 |
| compound 4 | 100 | 23 ± 1*** | 64.6 |
| compound 7 | 100 | 38 ± 3** | 41.5 |
| compound 11 | 100 | 27 ± 1*** | 58.5 |
| compound 12 | 100 | 35 ± 3*** | 46.2 |
| Tolubutamide | 50 | 53 ± 4 | 18.5 |
| control | — | 57 ± 4 | — |
| compound 15 | 100 | 30 ± 1*** | 47.4 |
| compound 16 | 100 | 30 ± 1*** | 47.4 |
| compound 17 | 100 | 30 ± 1*** | 47.4 |
| compound 18 | 100 | 30 ± 1*** | 47.4 |
| compound 21 | 100 | 35 ± 2** | 38.6 |
| compound 23 | 100 | 38 ± 2** | 33.3 |
| compound 24 | 100 | 30 ± 1*** | 47.4 |
| compound 25 | 100 | 33 ± 2*** | 42.1 |
| compound 26 | 100 | 37 ± 1** | 35.1 |
| compound 29 | 100 | 43 ± 3* | 24.6 |

TABLE 5

| Test Compound | Dosage (mg/kg) | Serum Free Fatty Acid Level (mEq/l) | Decrease (%) |
|---|---|---|---|
| control | — | 0.53 ± 0.03 | — |
| compound 2 | 100 | 0.25 ± 0.03*** | 52.8 |
| compound 4 | 100 | 0.27 ± 0.02*** | 49.1 |
| compound 11 | 100 | 0.34 ± 0.01*** | 35.8 |
| compound 12 | 100 | 0.37 ± 0.03** | 30.2 |
| Tolubutamide | 50 | 0.44 ± 0.02* | 15.7 |
| control | — | 0.52 ± 0.03 | — |
| compound 15 | 100 | 0.44 ± 0.02* | 15.4 |
| compound 18 | 100 | 0.42 ± 0.02** | 19.2 |
| compound 21 | 100 | 0.44 ± 0.02* | 15.2 |
| compound 24 | 100 | 0.45 ± 0.01* | 13.5 |

TABLE 6

| Test Compound | Dosage (mg/kg) | Total Serum Cholesterol Level (mg/dl) | Decrease (%) |
|---|---|---|---|
| control | — | 44 ± 2 | — |
| compound 4 | 100 | 39 ± 1* | 11.4 |

TABLE 6-continued

| Test Compound | Dosage (mg/kg) | Total Serum Cholesterol Level (mg/dl) | Decrease (%) |
| --- | --- | --- | --- |
| compound 11 | 100 | 39 ± 1* | 11.4 |
| compound 12 | 100 | 39 ± 1* | 11.4 |
| Tolubutamide | 50 | 46 ± 1 | −4.5 |
| control | — | 41 ± 1 | — |
| compound 15 | 100 | 33 ± 1*** | 19.5 |
| compound 16 | 100 | 33 ± 2** | 19.5 |
| compound 17 | 100 | 37 ± 1* | 9.8 |
| compound 18 | 100 | 34 ± 1*** | 17.1 |
| compound 21 | 100 | 36 ± 1** | 12.2 |
| compound 24 | 100 | 36 ± 1** | 12.2 |
| compound 25 | 100 | 36 ± 1** | 12.2 |
| compound 26 | 100 | 37 ± 1** | 9.8 |
| compound 29 | 100 | 36 ± 1** | 12.2 |

TABLE 7

| Test Compound | Dosage (mg/kg) | Serum Phospholipid Level (mg/dl) | Decrease (%) |
| --- | --- | --- | --- |
| control | — | 79 ± 2 | — |
| compound 2 | 100 | 59 ± 1*** | 25.3 |
| compound 4 | 100 | 58 ± 1*** | 26.6 |
| compound 7 | 100 | 66 ± 2*** | 16.5 |
| compound 11 | 100 | 60 ± 2*** | 24.1 |
| compound 12 | 100 | 61 ± 2*** | 22.8 |
| Tolubutamide | 50 | 75 ± 2 | 5.1 |
| control | — | 72 ± 2 | — |
| compound 15 | 100 | 52 ± 1*** | 27.8 |
| compound 16 | 100 | 54 ± 1*** | 25.0 |
| compound 17 | 100 | 58 ± 1*** | 19.4 |
| compound 18 | 100 | 56 ± 1*** | 22.2 |
| compound 21 | 100 | 57 ± 1*** | 20.8 |
| compound 23 | 100 | 65 ± 2* | 9.7 |
| compound 24 | 100 | 56 ± 1*** | 22.2 |
| compound 25 | 100 | 57 ± 2*** | 20.8 |
| compound 26 | 100 | 58 ± 1*** | 19.4 |
| compound 29 | 100 | 58 ± 1*** | 19.4 |

As shown by the above-mentioned results, the imidazolidinetrione derivatives of the present invention have excellent hypoglycemic and hypolipidemic effects.

The relationship between doses of compound 2 and decrease of blood glucose level show that the compounds of the invention are extremely useful as drugs to improve severe hyperglycemia, since even at high doses, they maintain the blood sugar at nearly normal levels, without excessive hypoglycemia caused by Tolubutamide.

Therefore, the compounds are not only useful as antidiabetics but also as drugs for various diseases caused by diabetes, e.g. diabetic angiopathy, such as diabetic arteriosclerosis, diabetic retinitis, diabetic nephropathy, diabetic neurosis and diabetic microangiopathy. Since the compounds of the invention are different type drugs from insulin as mentioned above, they are especially useful as drugs for noninsulin-dependent (type-II) diabetes mellitus.

The compounds of the invention also have hypolipidemic effects, which makes them useful in treating hyperlipidemia, and in the treatment or the prevention of various diseases caused by hyperlipidemia, such as arteriosclerosis, nephrosis, hypertension, diabetes or obesity.

Since an increase of blood lipids is induced by an abnormal metabolism of glucose or a lowering of lipoprotein-lipase activity caused by diabetes, hyperlipidemia is often caused together with diabetes. Therefore, the compounds of the present invention having both hypoglycemic and hypolipidemic effects are useful as drugs for such complications.

The compounds of the present invention have low toxicity and great safety, so that their long-term continuous administration and oral use are possible.

The compounds of the present invention may be made into pharmaceutical compositions by combination with appropriate medicinal carriers or diluents, and may be formulated into preparations in solid, semisolid, liquid or gaseous form such as tablets, capsules, powders, granules, ointments, solutions, suppositories, injections, inhalants, aerosols and cataplasms in usual ways for oral or parenteral administrations.

In pharmaceutical dosage forms, the compounds of the present invention may be used in the form of their pharmaceutically acceptable salts, and also may be used alone or on appropriate association, as well as in combination with other pharmaceutically active components.

In case of oral preparations, the compounds may be used alone or combined with appropriate additives to make tablets, powders, granules or capsules, e.g. with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethylcellulose; with lubricants such as talc or magnesium stearate; and if desired, with diluents, buffering agents, moistening agents, preservatives and flavoring agents.

Furthermore, they may be made into suppositories by mixing with a variety of bases such as emulsifying bases or water-soluble bases.

The compounds of the present invention may be formulated into preparations for injections by dissolving, suspending or emulsifying them in aqueous or non-aqueous solvents, such as vegetable oil, synthetic aliphatic acid glycerides, esters of higher aliphatic acids or propylene glycol; and if desired, with conventional additives such as solubilizers, isotonic agents, suspending agents, emulsifying agents, stabilizers and preservatives.

In case of inhalations or aerosol preparations, the compounds of the invention in the form of a liquid or minute powder may be filled up in an aerosol container with gas or liquid spraying agents, and if desired, with conventional adjuvants such as humidifying agents added thereto. They may also be applied as pharmaceuticals for non-pressurized preparation such as in a nebulizer or an atomizer.

Cataplasms may be prepared by mixing the compounds with mentha oil, concentrated glycerin, kaolin or other suitable additives.

The desirable dose of the imidazolidinetrione derivatives of the present invention varies with the subject, drug form, method and period of administration. However, in order to obtain desirable effects, generally it is recommended to administer orally 1 to 1000 mg, preferably 5 to 600 mg daily. Unit preparations containing appropriate amounts of the compounds of the present invention are also recommended for administration in 1 to several units daily.

In case of parenteral administrations e.g. injections, doses of the compounds in the order of one tenth to one third of the above dose are preferable as daily doses.

Some prescriptions of the pharmaceutical compositions are shown below as examples which contain the compounds of the present invention as active ingredients.

| Prescription example 1 (tablet) | |
| --- | --- |
| Component | Content in a tablet (mg) |
| compound of the invention | 100 |
| lactose | 130 |
| corn starch | 40 |
| magnesium stearate | 10 |
| Total | 280 mg |

| Prescription example 2 (capsule) | |
| --- | --- |
| Component | Content in a capsule (mg) |
| compound of the invention | 50 |
| lactose | 250 |
| Total | 300 mg |

| Prescription example 3 (injection) | |
| --- | --- |
| Component | Content in an ampule (mg) |
| compound of the invention | 10 |
| sodium chloride | proper amount |
| distilled water for injection | proper amount |
| Total | 1 ml |

| Prescription example 4 (ointment) | |
| --- | --- |
| Component | Weight (g) |
| compound of the invention | 1 |
| emulsified wax | 30 |
| white petrolatum | 50 |
| liquid paraffin | 20 |
| Total | 101 g |

| Prescription example 5 (suppository) | |
| --- | --- |
| Component | Content in a suppository (mg) |
| compound of the invention | 20 |
| cacao butter | 1980 |
| Total | 2000 mg |

What is claimed is:

1. A pharmaceutical composition for use in treating diabetes and hyperlipidemia comprising as an active ingredient an effective amount of at least one imidazolidinetrione derivative of the formula:

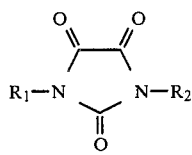

wherein each of $R_1$ and $R_2$, which may be the same or different, is hydrogen, an alkyl group, a cycloalkyl group or

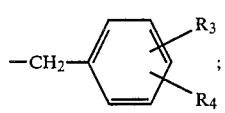

and each of $R_3$ and $R_4$, which may be the same or different, is hydrogen, halogen, a nitro group, a lower alkyl group or a lower alkoxy group, or a pharmaceutically acceptable salt thereof, and an inert carrier or diluent.

2. A pharmaceutical composition according to claim 1, which is formulated into a form suitable for oral administration.

3. A pharmaceutical composition according to claim 1, which is formulated into a form suitable for parenteral administration.

4. A method for treating diabetes which comprises administering to a subject an effective hypoglycemic amount of an imidazolidinetrione derivative of the formula

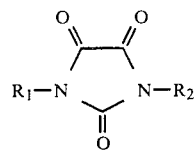

wherein each of $R_1$ and $R_2$, which may be the same or different, is hydrogen, an alkyl group, a cycloalkyl group or

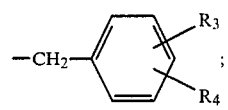

and each of $R_3$ and $R_4$, which may be the same or different, is hydrogen, halogen, a nitro group, a lower alkyl group or a lower alkoxy group.

5. A method for treating hyperlipidemia which comprises administering to a subject an effective hypolipidemic amount of an imidazolidinetrione derivative of the formula

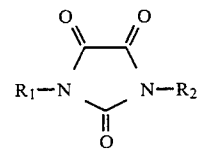

wherein each of $R_1$ and $R_2$, which may be the same or different, is hydrogen, an alkyl group, a cycloalkyl group or

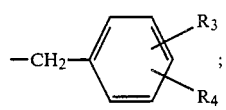

and each of $R_3$ and $R_4$, which may be the same or different, is hydrogen, halogen, a nitro group, a lower alkyl group or a lower alkoxy group.

6. The method of claim 4, wherein said imidazolidinetrione derivative is administered orally in a dosage of 1 to 1000 mg daily.

7. The method of claim 5, wherein said imidazolidinetrione derivative is administered orally in a dosage of 1 to 1000 mg daily.

8. The method of claim 4, wherein said imidazolidinetrione derivative is administered parenterally in a dosage of 0.1 to 333 mg daily.

9. The method of claim 5, wherein said imidazolidinetrione derivative is administered parenterally in a dosage of 0.1 to 333 mg daily.